United States Patent [19]

Vassiliou et al.

[11] Patent Number: 5,801,273
[45] Date of Patent: Sep. 1, 1998

[54] METHODS AND DEVICES FOR CONTROLLING THE REACTION RATE OF A HYDROCARBON TO AN INTERMEDIATE OXIDATION PRODUCT BY PRESSURE DROP ADJUSTMENTS

[75] Inventors: Eustathios Vassiliou, Newark, Del.; Mark W. Dassel, Indianola, Wash.; David C. DeCoster, Buckley, Wash.; Ader M. Rostami, Bainbridge Island, Wash.; Sharon M. Aldrich, Poulsbo, Wash.

[73] Assignee: Twenty-First Century Research Corporation, Newark, Del.

[21] Appl. No.: 859,985

[22] Filed: May 21, 1997

[51] Int. Cl.$^6$ .................................................. C07C 51/16
[52] U.S. Cl. ............... 562/413; 562/512.4; 562/528; 562/538; 562/543; 562/529; 568/357; 568/358; 568/570; 568/836
[58] Field of Search ............... 562/413, 512.4, 562/528, 538, 543, 529; 568/357, 358, 570, 836

[56] References Cited

U.S. PATENT DOCUMENTS

| | | | |
|---|---|---|---|
| 1,121,532 | 12/1914 | Newberry . | |
| 2,014,044 | 9/1935 | Haswell | 75/17 |
| 2,223,493 | 12/1940 | Loder | 260/537 |
| 2,223,494 | 12/1940 | Loder | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon | 252/413 |
| 3,231,608 | 1/1966 | Kollar | 260/533 |
| 3,234,271 | 2/1966 | Barker | 260/531 |
| 3,290,369 | 12/1966 | Bonfield | 26/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,928,005 | 12/1975 | Laslo | 55/73 |
| 3,932,513 | 1/1976 | Russell | 260/586 |
| 3,946,074 | 3/1976 | Paasen et al. | 260/586 P |
| 3,957,876 | 5/1976 | Rapoport et al. | 260/586 |
| 3,987,100 | 10/1976 | Barnette et al. | 260/586 |
| 3,987,808 | 10/1976 | Carbonell et al. | 137/3 |
| 4,039,304 | 8/1977 | Bechthold et al. | 55/10 |
| 4,055,600 | 10/1977 | Langley et al. | 260/586 P |
| 4,065,527 | 12/1977 | Graber | 261/79 A |
| 4,308,037 | 12/1981 | Meissner et al. | 55/10 |
| 4,361,965 | 12/1982 | Goumondy et al. | 34/57 |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |

FOREIGN PATENT DOCUMENTS

| | | | |
|---|---|---|---|
| 0439007A2 | 7/1991 | European Pat. Off. | C07C 68/38 |
| 0751105A2 | 1/1997 | European Pat. Off. | C08B 33/00 |
| 4426132A1 | 1/1996 | Germany . | |
| 415172 | 8/1934 | United Kingdom | 8132 33 |
| 738808 | 10/1955 | United Kingdom | 2/3 |
| 1143213 | 2/1969 | United Kingdom | 51/16 |
| WO96/03365 | 2/1996 | WIPO . | |

OTHER PUBLICATIONS

U.S. application No. 08/587,967, Mark W. Dassel and Eustathios Vassiliou, filed Jan. 17, 1996.
U.S. application No. 08/812,847, Mark W. Dassel, Eustathios Vassiliou, David C. DeCoster, Ader M. Rostami, and Sharon M. Aldrich, filed Mar. 6, 1997.
U.S. application No. 08/824,992, Mark W. Dassel, David C. DeCoster, Ader M. Rostami, Sharon M. Aldrich, and Eustathios Vassiliou, filed Mar. 27, 1995.
U.S. application No. 08/477,195, Mark W. Dassel and Eustathios Vassiliou, filed Jun. 7, 1995.
E. Sorribes et al., "Formación de neuvas fases en el proceso de obtención de ácido adípico: causas y efectos que provocan,"*Rev. R. Acad. Cien. Exactas, Fis. Nat. Madrid* (1987), 81(1), 233–5 (+English language translation).

*Primary Examiner*—Samuel Barts
*Attorney, Agent, or Firm*—Seed and Berry LLP

[57] ABSTRACT

Methods and devices for controlling the reaction rate of a hydrocarbon to an acid or other intermediate oxidation product by pressure drop rate adjustments. The pressure drop rate measurements are conducted at predetermined time intervals, after stopping the feeding and exiting of gases. The pressure drop at a predetermined time interval is measured or the time it takes for the pressure to drop by a certain degree. Adjustments are then made in one or more temperature, feeding rates of hydrocarbon, solvent, catalyst, promoter, and the like until the pressure drop rate and the reaction rate fall within desirable predetermined limits.

16 Claims, 1 Drawing Sheet

METHODS AND DEVICES FOR CONTROLLING THE REACTION RATE OF A HYDROCARBON TO AN INTERMEDIATE OXIDATION PRODUCT BY PRESSURE DROP ADJUSTMENTS

CROSS-REFERENCE TO RELATED APPLICATIONS

The present application claims the benefit of U.S. Provisional application Ser. No. 60/024,263 filed Aug. 21, 1996, which application is incorporated herein by reference in its entirety.

FIELD OF THE INVENTION

This invention relates to methods of making intermediate oxidation products, such as acids, ketones, alcohols, hydroperoxides, for example, and in general organic compounds different than carbon monoxide and carbon dioxide, by oxidizing a hydrocarbon with a gas containing an oxidant, preferably oxygen.

BACKGROUND OF THE INVENTION

There is a plethora of references (both patents and literature articles) dealing with the formation of intermediate oxidation products, one of the most important being adipic acid. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is important to note that most, if not all, studies on the Direct Synthesis Process have been conducted in a batch mode, literally or for all practical purposes.

There is a plethora of references dealing with oxidation of organic compounds to produce acids, such as, for example, adipic acid.

The following references, among the plethora of others, may be considered as representative of oxidation processes relative to the preparation of diacids.

U.S. Pat. No. 5,463,119 (Kollar) discloses a process for the oxidative preparation of $C_5$–$C_8$ aliphatic dibasic acids by (1) reacting,
  (a) at least one saturated cycloaliphatic hydrocarbon having from 5 to 8 ring carbon atoms in the liquid phase and
  (b) an excess of oxygen gas or an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;

(2) removing the aliphatic dibasic acid; and (3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone.

The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture in the presence of
  (c) less than 1.5 moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and (2) isolating the C5–C8 aliphatic dibasic acid.

U.S. Pat. No. 5,221,800 (Park et al.) discloses a process for the manufacture of adipic acid is disclosed. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A 1 (Kysela et al.) discloses a method for dehydration of process acetic acid from the liquid-phase oxidation of cyclohexane with air, in the presence of cobalt salt as a catalyst after separation of the adipic acid by filtration and the cyclohexane phase by phase separation, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than about 0.3 to 0.7 wt %.

PCT Demand International Publication WO 96/03365 (Costantini et al.) discloses a method of recycling a cobalt-containing catalyst in a reaction involving the direct oxidation of cyclohexane into adipic acid using an oxygen containing gas. The method is characterized in that the reaction mixture, obtained in a preceding stage where the cyclohexane was oxidized into adipic acid, of which at least part of the intermediate oxidation products, such as cyclohexanol and cyclohexanone, the carboxylic acid and water has been separated and of which at least part of the adipic acid formed has been recovered by crystallization, undergoes at least one extraction operation using at least one cosolvent or a mixture comprising a cosolvent and a carboxylic acid. The method is also characterized by the separation of a mixture containing at least part of the cobalt catalyst, part of the carboxylic acid and optionally residual quantities of other compounds and a solution containing the co-solvent and at least part of the glutaric and succinic acids formed during the oxidation reaction, and the carboxylic acid.

None of the above references, or any other references known to the inventors disclose, suggest or imply, singly or in combination, oxidation reactions to intermediate oxidation products under reaction rate controlled conditions subject to the intricate and critical controls and requirements of the instant invention as described and claimed.

Our U.S. Pat. Nos. 5,580,531, 5,558,842, 5,502,245, and our co-pending applications 08/477,195 (filed Jun. 7, 1995), 08/587,967 (filed Jan. 12, 1996), and 08/620,974 (filed Mar. 25, 1996), all of which are incorporated herein by reference, describe methods and apparatuses relative to controlling reactions in atomized liquids.

Our co-pending application, Docket No. T-603, of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Acid by Making Phase-related Adjustments," filed on Mar. 6, 1997, and having a Ser. No. 08/812,847, is also incorporated herein by reference.

Our co-pending application, Docket No. T-701, of Mark W. Dassel, David C. DeCoster, Ader M. Rostami, Sharon M. Aldrich, and Eustathios Vassiliou, titled "Methods and Devices for Preparing Dibasic Acids," filed on Mar. 27, 1997, and having a Ser. No. 08/824,992 is also incorporated herein by reference.

All of the following patent applications, which were filed simultaneously with the present application are also incorporated herein by reference:

U.S. patent application Ser. No. 08/861,281, of Mark W. Dassel, Eustathios Vassiliou, David C. DeCoster, Ader M.

Rostami, and Sharon M. Aldrich, titled "Methods and Devices for Controlling the Reaction Rate of a Hydrocarbon to an Intermediate Oxidation Product by Monitoring Flow of Incoming and Outcoming Gases."

U.S. patent application Ser. No. 08/861,180, of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a Rate-Modulator."

U.S. patent application Ser. No. 08/861,176, of Mark W. Dassel, Eustathios Vassiliou, David C. DeCoster, and Ader M. Rostami, titled "Methods of Preparing an Intermediate Oxidation Product from a Hydrocarbon by Utilizing an Activated Initiator."

U.S. patent application Ser. No. 08/859,890, of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements."

U.S. patent application Ser. No. 08/861,210, of Eustathios Vassiliou, Ader M. Rostami, David C. DeCoster, and Mark W. Dassel, titled "Pseudo-Plug-Flow Reactor."

SUMMARY OF THE INVENTION

As aforementioned, this invention relates to methods of making intermediate oxidation products, such as acids, for example, by oxidizing a hydrocarbon with a gas containing an oxidant, preferably oxygen. More particularly, it relates to a method of controlling the oxidation of a hydrocarbon to an intermediate oxidation product in a reaction zone comprising the steps of:

(a) feeding a predetermined amount or rate of a gaseous oxidant and a predetermined amount or rate of hydrocarbon into the reaction zone, the reaction zone attaining a first pressure;

(b) measuring the rate of pressure-drop during the reaction by conducting at least one step of
   (i) allowing the gaseous oxidant to cause a reaction in a manner that the reaction zone attains a second pressure, lower than the first pressure, at least partially resulting from the reaction;
   (ii) allowing the gaseous oxidant to cause a reaction and measuring the pressure drop within a predetermined interval of time;

(c) adjusting the rate of the pressure-drop within a desired range by regulating a parameter in the reaction zone selected from a group consisting of temperature, feed of gaseous oxidant, composition of gaseous oxidant, pressure, feed of hydrocarbon, feed of solvent, feed of catalyst, feed of promoter, and a combination thereof;

(d) repeating steps (a) to (c);

(e) continuing repeating steps (a) to (c).

Preferably the hydrocarbon is a cyclic aliphatic hydrocarbon, more preferably having 5 to 12 carbon atoms, and even more preferably, the cyclic aliphatic hydrocarbon is cyclohexane.

In other preferred embodiments, the hydrocarbon is a methylated aromatic hydrocarbon. It is more preferred that the methylated aromatic hydrocarbon is toluene and the intermediate oxidation product is benzoic acid.

In still other embodiments, the methylated aromatic hydrocarbon is selected from a group consisting of o-xylene, m-xylene, p-xylene, and a mixture thereof, and the intermediate oxidation product is selected from a group consisting of o-phthalic acid, isophthalic acid, terephthalic acid, and a mixture thereof, respectively.

The preferred gaseous oxidant comprises oxygen.

The hydrocarbon may be mixed and/or contain at least one ingredient selected from a group consisting of solvent, catalyst, promoter, and a mixture thereof, and it may be in an atomized form within the reaction zone. Of course, it may also be in stirred form with a stirrer, or in a recirculation form inside and outside the reaction zone.

Further, the instant invention pertains to a method, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

The instant invention, also relates to a device for controlling the oxidation of a hydrocarbon to an intermediate oxidation product comprising:

a reaction chamber;

oxidant feeding means connected to the reaction chamber for feeding predetermined amounts or rates of a gaseous oxidant into said reaction chamber;

at least one of
   temperature monitoring means for monitoring the temperature in said reaction chamber;
   hydrocarbon feeding means connected to the reaction chamber for feeding a predetermined amount or rate of a hydrocarbon into said reaction chamber;
   solvent feeding means connected to the reaction chamber for feeding a predetermined amount or rate of a solvent into said reaction chamber;
   catalyst feeding means connected to the reaction chamber for feeding a predetermined amount or rate of a catalyst into said reaction chamber;
   promoter feeding means connected to the reaction chamber for feeding a predetermined amount or rate of a promoter into said reaction chamber;

pressure monitoring means connected to the reaction chamber for measuring pressure inside the reaction chamber;

interrupting means for stopping temporarily in predetermined intervals feeding of gases into the reaction chamber and exiting of gases from the reaction chamber; and a controller connected to the pressure monitoring means for obtaining pressure related information from said pressure monitoring means; the controller being programmed to calculate pressure drop rate during said predetermined intervals, the controller also being connected to the at least one temperature monitoring means, the oxidant feeding means, the hydrocarbon feeding means, the solvent feeding means, the catalyst feeding means, and the promoter feeding means; the controller being programmed to adjust at least one of said temperature monitoring means, oxidant feeding means, hydrocarbon feeding means, solvent feeding means, catalyst feeding means, and promoter feeding means, in a manner to maintain the pressure drop rate within a desired range.

The device of the instant invention may also comprise recycle feeding means for recycling matter after at least partial removal of reaction products.

Preferably, at least two of said oxidant feeding means, hydrocarbon feeding means, solvent feeding means, catalyst feeding means, and promoter feeding means are combined to one combination means.

The reaction chamber may be at least part of a stirred-tank reactor or at least part of an atomization reactor.

BRIEF DESCRIPTION OF THE DRAWING

The reader's understanding of this invention will be enhanced by reference to the following detailed description taken in combination with the drawing figure, wherein.

DETAILED DESCRIPTION OF THE INVENTION

Figure 1:
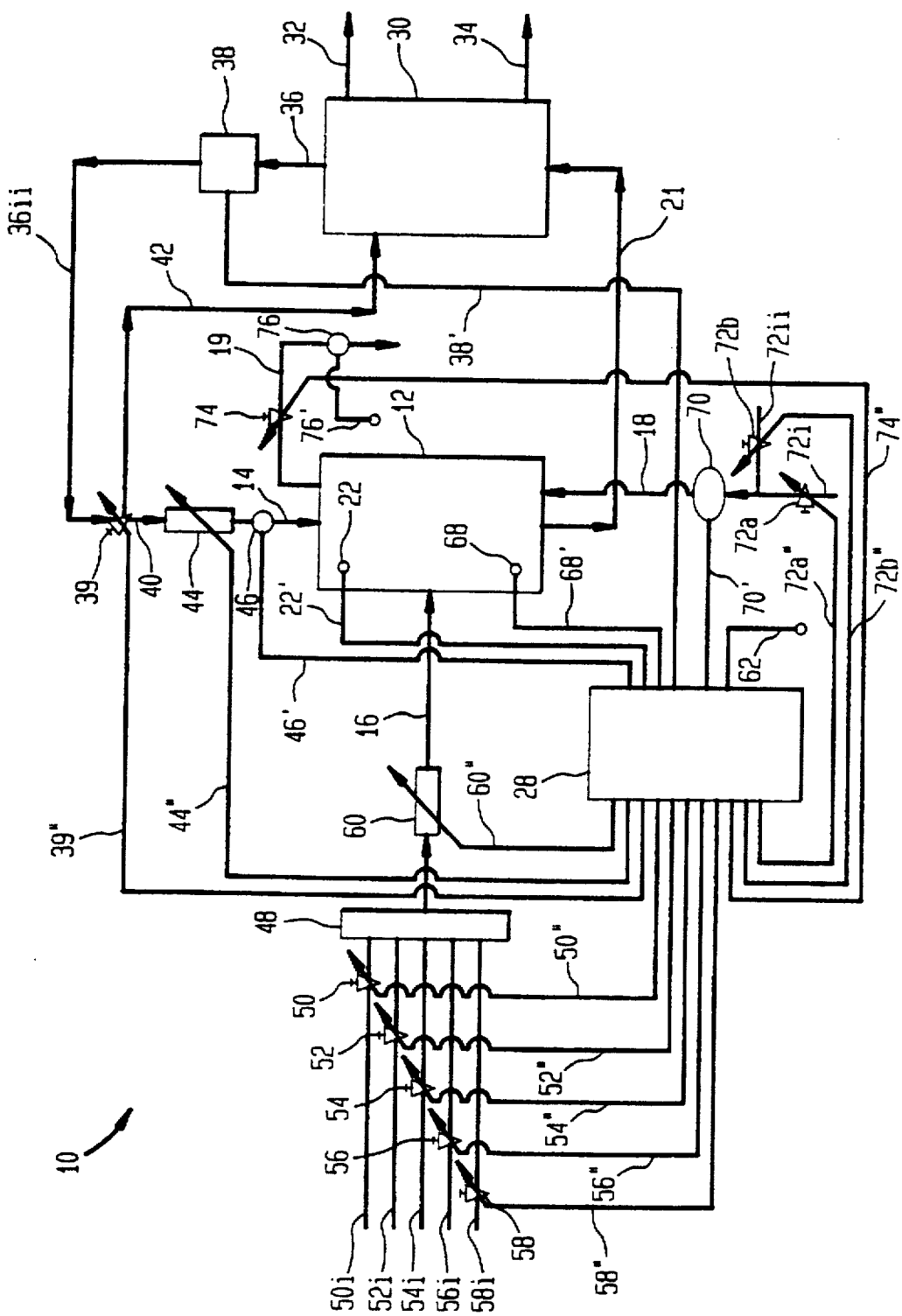
FIG. 1 illustrates schematically a preferred embodiment of the present invention.

As mentioned earlier, this invention relates to methods of making intermediate oxidation products, such as acids, for example, by oxidizing a hydrocarbon with a gas containing an oxidant, preferably oxygen.

The reaction rate in an oxidation such as for example the direct oxidation of cyclohexane to adipic acid, is very important for a number of reasons, among which productivity is of major significance. High productivity may be also compromised with lower temperatures, which usually result in better selectivity and yield. Since in a process productivity has usually to be compromised with selectivity and yield, a predetermined optimal solution has to be found, depending on each particular occasion. Thus, control of the reaction rate during an oxidation is of utmost importance.

According to this invention, pressure drop rate monitoring and control, achieves a fast and easy way to control the reaction rate within desirable predetermined limits.

To measure the pressure drop rate, a number of different techniques may be used, among which the most preferred ones are:

after the reaction chamber is pressurized, the feeding and exiting of gases is stopped temporarily, and the time for the initial pressure (first pressure) to drop to a second predetermined pressure level is measured; and after the reaction chamber is pressurized to a first pressure, the feeding and exiting of gases is stopped and a second pressure attained in predetermined period of time is measured.

The above measurements and operations may be made in a continuous basis, or a sporadic basis, or in any desirable predetermined pattern.

A preferred embodiment of this invention is illustrated in FIG. 1. In FIG. 1, there is depicted a device or continuous reactor system 10 comprising a reaction chamber 12. The reaction chamber 12 may be any type of reaction chamber, according to the instant invention. Examples of reaction chambers are atomization reactors as described for example in our U.S. Pat. Nos. 5,502,245, 5,580,531, 5,558,842, and our co-pending applications 08/477,195 (filed Jun. 7, 1995), 08/587,967 (filed Jan. 17, 1996), and 08/620,974 (filed Mar. 25, 1996), all of which are incorporated herein by reference, stirred tank reactors, recirculation reactors (in which the stirring is conducted by recirculation, and they are included in the stirred tank reactor category as far as this invention is concerned), and the like. A recycle feeding or inlet line 14, a new raw material feeding or inlet line 16, a gaseous oxidant feeding or inlet line 18, a gas outlet line 19, a predominantly non-gaseous outlet line 21, means for measuring temperature, such as thermocouple 22 for example, and means for measuring pressure, such as gauge or transducer 68 for example, are connected to the reaction chamber 12. Inlet line 18 is fed by merging lines 72i and 72ii through flowmeter 70 and valves 72a and 72b, which valves are controlled by the computerized controller 28, through output lines 72a" and 72b", respectively. In line 19, there are disposed valve 74 and flowmeter 76. Flowmeter 76 is connected to the computerized controller 28 through input line 76' (not shown connected for purposes of clarity) to give gas flow information to said computerized controller 28. The computerized controller 28 controls valve 74 through output line 74".

Other elements, commonly used with reaction chambers, such as condensers and the like, for example, in line 19 before or after the valve 74 or flowmeter 76, are not shown in FIG. 1 for purposes of clarity. Also, optional means for conducting chemical analysis of the contents of the reaction chamber 12 are not shown, also for purposes of clarity. The optional means (not shown) for conducting chemical analysis of the contents of the reaction chamber 12, preferably, also provide ingredient content information to the computerized controller 28. The inlet, outlet, input or output lines may be positioned in any suitable location of the reaction chamber 12. The words "inlet" and "outlet" are used for lines which feed or withdraw materials, respectively, while the words "input" and "output" are used for lines which provide information to the computerized controller 28, or are utilized by the controller to control other elements of the device, respectively.

The predominantly non-gas outlet line 21 leads to a material management station 30, at which the products of reaction, any by-products, non-converted raw materials, etc., are separated by well known to the art techniques. Such techniques may involve filtration, distillation, crystallization, other types of separation, evaporation, cooling, heating, storage, decontamination, incineration, disposal, etc.

The desired product of reaction follows product path 32, the non-recyclable by-products follow non-recyclables path 34, while recyclable materials follow recyclables line 36, which line 36 leads to an analytical apparatus 38 for analysis of the contents of the recyclables. The analytical apparatus 38 samples and analyzes the recyclables before they enter line 36ii. Line 36 may comprise one or a plurality of lines, depending of the nature of the recyclables. Some of these lines may even circumvent the analytical apparatus 38, if so desired (if for example the content of the recyclable material under consideration is known or previously determined by any of well known to the art techniques).

The recyclables follow line 36ii, which leads to a three way valve 39, in a manner that the recyclables may follow line 40 or 42 or both in any desired ratio. Line 42 leads back to the material management station 30 for storage or retention or re-work, or the like, while line 40 leads to a first heat exchanger (including cooler or heater or the like) 44.

The 3 way valve 39 is controlled by the computerized controller 28 through output line 39". Similarly, the heat exchanger 44 is controlled by the computerized controller 28 through output line 44". Preferably one or more input lines (not shown for purposes of clarity) provide temperature information to the computerized controller 28 regarding the recyclables as they enter end exit the heat exchanger 44.

The recyclables enter the reaction chamber 12 after they pass through flowmeter 46, which gives recyclables flow data to the computerized controller 28 through input line 46'.

Input lines 22' and 68' feed the computerized controller 28 with temperature information and pressure information, respectively, within the reaction chamber 28. More lines may be necessary, depending on the information required in each particular case.

Flow regulation valves 50, 52, 54, 56, and 58 are connected to inlet lines 50i, 52i, 54i, 56i, and 58i, which provide hydrocarbon, solvent, catalyst, promoter, and other adjuncts, respectively, to a pre-mixing vessel 48. The premixing vessel 48 is preferably of small size and positioned in a way that all its contents are moving out of it and through line 16, so that if more than one phase is present, there is no accumulation of a particular phase in the pre-mixing vessel. Pre-mixing vessel 48 is connected with a second heat exchanger (including cooler or heater or the like) 60, which in turn is connected to the reaction chamber 12. The inlet lines 50i, 52i, 54i, 56i, and 58i, may however be directly connected to the second heat exchanger 60 or to the reaction chamber 12.

The inlet lines 50i, 52i, 54i, 56i, and 58I may be heated separately with their own individual heaters (not shown for purposes of clarity), which heaters are preferably controlled by controller 28. With this arrangement, formation of two phases may be avoided in premixing vessel 48. The heater 60 may then be omitted or it may be used for fine tuning of the final temperature.

Flow regulation valves 50, 52, 54, 56, and 58 are controlled by the computerized controller 28 through output lines 50", 52", 54", 56", and 58", respectively. A number of flowmeters (not shown for purposes of clarity) connected to lines 50i, 52i, 54i, 56i, and 58i, provide flow information regarding hydrocarbon, solvent, catalyst, promoter, and other adjuncts, to the computerized controller 28 through multiple input line 62.

The reaction chamber 12 may be heated or cooled by heating or cooling means (not shown) well known to the art.

The lines 14 and 16 may merge together into a single line (not shown), and feed the reaction chamber through said single line.

In operation of this embodiment, hydrocarbon, solvent, catalyst, promoter and any other desired adjuncts are added to the pre-mixing vessel 48, where they are mixed together. The pre-mixing vessel is small enough and positioned in a manner that if there is phase separation, no particular phase remains behind, but all phases are commingled and they proceed through the second heat exchanger 60 and to the reaction chamber 12 through line 16. The feed rates of the new raw materials fed through lines 50i, 52i, 54i, 56i, and 58i depend on the feed rates of the recyclables fed to the reaction chamber 12 through recycle feeding line 14. Information regarding the analytical results from the analytical apparatus 38 is provided to the computerized controller 28, which combines this information with the information from the flowmeter 46 and the information from the flowmeters (not shown) of lines 50i, 52i, 54i, 56i, and 58i, and calculates the total feed rate of each individual ingredient entering the reaction chamber 12.

The computerized controller preferably gives precedence to the recyclables, and then it adjusts each of the valves 50, 52, 54, 56, and 58 through output lines 50", 52", 54", 56", and 58", respectively, in a manner that the total feed rate of each individual ingredient entering the reaction chamber 12 has a desired value. The desired value of each ingredient feed rate is preferably adjusted toward a desired range of values of pressure drop, as it will be discussed later.

Of course, when the operation starts, there are no recyclable materials, so that only new raw materials start entering the system through one or more of lines 50i, 52i, 54i, 56i, and 58i, and finally enter the reaction chamber 12 through line 16. During starting the operation, the different feed rates of new raw materials are arranged so that the pressure drop rate falls within the predetermined range. An initiation period, before the reaction starts, has to be taken into account. Preferably, the reaction is driven toward formation of a single phase, as described for example in our co-pending patent application Docket No. T-603, of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Acid by Making Phase-related Adjustments," filed on Mar. 6, 1997, having Ser. No. 08/812,847, which is incorporated herein by reference.

The balance of materials is also preferably arranged to be such that when water starts being formed during the oxidation, no second phase is formed. This, however is not necessary for the practice of the instant invention. The amount of water formed depends on the conversion taking place when the system attains a steady state. The more solvent, acetic acid for example, is present at this steady state, the more water may be withstood by the system without formation of a second phase. Since the formation of water is substantially unavoidable when a hydrocarbon is oxidized, and in some respects its presence may even be desirable (for at least partial hydrolysis of undesirable ester by-products, for example), it is preferable to work at a steady state which can contain at least a predetermined content of water without the formation of a second phase. Removal of water in any step of the process, if necessary or desired, may be achieved by a number of ways, including for example distillation, addition of acid anhydrides, and other well known to the art methods.

The more hydrocarbon, cyclohexane for example, is present in the reaction chamber the higher the potential of formation of a second phase. At the same time, if too little hydrocarbon is present, the reaction starts starving from lack of hydrocarbon. According to the instant invention, the amount of hydrocarbon present in the steady state is preferably just above the point at which starvation is observed. "Just above" starvation means preferably between 0% to 20% above starvation, and more preferably 5% to 20% above starvation.

At the same time that the above mentioned ingredients enter the reaction chamber 12, a gas containing an oxidant, preferably oxygen, enter the reaction chamber through the gaseous oxidant feeding line 18, and it comes in contact with the mixture containing the hydrocarbon. Oxidant may be recirculated in the system for better sparging. It is preferable that the oxidant for recirculation is obtained at a point before valve 74 (between valve 74 and the reaction chamber 12).

The reaction temperature or first temperature is monitored by one or more thermocouples, such as thermocouples 22 for example, which provides temperature information to the controller 28. The pressure in the reaction chamber 12 is monitored by the pressure gauge or transducer 68, which provides pressure information the computerized controller 28 through input line 68'.

The computerized controller 28, based on this temperature information adjusts the first and second heat exchangers through output lines 44" and 60", respectively, in a manner that in combination with the heat released by the reaction, and the thermal characteristics of the reaction chamber 12, the temperature attains and maintains a desired value. In order to lower the temperature in the reaction chamber, the heat exchangers are adjusted to lower the temperatures in lines 14 and 16. In addition to or instead of this, the reaction chamber itself may be provided with heating and/or cooling means (not shown for purposes of clarity, but well known to the art), controlled by the computerized controller 28, so that the temperature attains and maintains the desired value. The desired value may, of course, be a desired range of values.

When the temperature is raised, the potential for formation of a single phase is increased, and the rate of reaction is increased. However, the selectivity to the desired final product may suffer. Therefore, a balance among rate of reaction, selectivity, and temperature has to be decided. This decision may depend on the particular circumstances, and may be based on economical, safety, environmental, and other considerations.

Thus, the temperature may preferably be adjusted through the computerized controller 28 within the desired range in a manner to promote the formation and/or maintenance of a single phase. If a single phase already exists, the temperature may preferably be reduced to the minimum limit of the desired range, and maintained there, if this decrease in temperature does not cause the formation of a second phase.

For constant purge rates of non-condensibles from the reaction chamber 12, lowering the pressure within the reaction chamber 12 moves the system toward a single phase formation since more hydrocarbon, cyclohexane for example, evaporates and the content of hydrocarbon in the liquid decreases.

Increasing gas sparging in the case of a stirred-tank reaction chamber, or in general the flow of the gaseous oxidant in the case of an atomization reactor (described for example in our aforementioned patents and patent applications) has a similar effect as lowering the pressure.

Lowering the conversion, or hold-up time in the reaction chamber 12, decreases the amount of water formed, which decrease has as an effect to promote the formation of a single phase.

Lowering the amount or rate of catalyst, cobalt acetate for example, also promotes the formation of a single phase. It should be noted here that when cobaltous acetate tetrahydrate is used, water is necessarily introduced, corresponding to the water of hydration of the cobaltous acetate salt.

According to the instant invention, the pressure is monitored by the pressure monitor 68, and the information is fed to the computerized controller 28 through input line 68'.

A gas comprising oxidant, preferably oxygen enters the system through line 18, which line 18 is fed from lines 72i and 72ii, which in turn comprise valves 72a and 72b, respectively. Valves 72a" and 72b" are controlled by the computerized controller 28 through output lines 72a" and 72b", respectively. Although it is preferable for the line 18 to be fed by the two lines 72i and 72ii, it may also be fed by just one of the two lines, as long as that one line comprises oxidant, preferably oxygen. In the particular case of this example, line 72i, conducts a gas containing oxidant, such as air for example, and line 72ii conducts oxidant, such as oxygen for example. The exact content of oxidant in the lines may assume any values, as long as a controlled amount or rate of oxidant may be fed to line 18. It is preferred that line 72i conducts air and line 72ii conducts oxygen.

When the pressure inside the reaction chamber reaches a desired first pressure value, the valves 72a, 72b and 74 are caused to close by the controller 28, and the first pressure is allowed to drop to a second pressure value, preferably close to the first pressure value. The time interval between the two pressures determines the pressure drop rate. Alternatively, the pressure drop rate may be determined by measuring the first pressure and the pressure attained within a predetermined time interval. The time interval is preferably in the range of 1/5 to 1/50 of the hold up time in the reaction chamber.

The determination of the pressure drop rate is very important because it is a measure of the reaction rate. In turn, the reaction rate is important because of higher productivity. Also with higher rates, lower temperatures may be afforded which may result in better selectivity and yield. Of course a balance should be selected and exercised between selectivity/yield and reaction rate.

Carbon dioxide and carbon monoxide monitors (not shown) in the offgases are also preferably utilized because they are indicative of selectivity and yield. An oxygen monitor (not shown) is also preferably used for determination of the oxygen content within the reaction chamber 12 or in the off gases.

When the determination of drop rate is completed, valve 72b is opened for the missing oxidant, preferably oxygen, to enter the reaction chamber, and raise the pressure to attain its first pressure value again. Then it is closed, and the same process may be followed for a number of cycles. In turn, valve 74 is opened for off gases to leave the system and new supply of gas is provided to the reaction chamber through lines 72i and 72ii, after 72a and 72b open, for the pressure to attain again its first pressure value. Measurements of flow through the flowmeters 70 and 76 are useful for information sent to the computerized controller 28, which adjusts in turn 72a, 72b and 74 appropriately.

In place or in addition to flowmeter 70, flowmeters (not shown) in both or one of lines 72i and 72ii may be used for more information.

Instead of the sequence of valve openings and closings described above any other sequence may be utilized as long as the pressure drop rate due to oxidant, preferably oxygen, consumption is measured. For example, in another embodiment of the present invention, oxidant may be entering the reaction chamber and simultaneously off gasses may be exiting the reaction chamber 12. At a predetermined point valves 74, 72a and 72b are closed, and the pressure drop rate is determined. After the pressure drop determination, the valves 74, 72a and 72b are opened again to an appropriate degree and the same process is repeated after a desired interval of time.

When the determination of pressure drop rate has been made by the computerized controller 28, action is taken to control said pressure drop rate, and in a parallel manner the reaction rate, to fall within a desired region.

If the measured pressure drop rate, or reaction rate, falls under the desired region, the computerized controller is for example preferably programmed to follow the following sequence of steps to raise the pressure drop rate. However, depending on the individual circumstances, the sequence may be changed, a number of steps may be omitted, or other steps added. If a step is proven to be ineffective during the operation, any action that was performed to perform the step may be reversed and the next step conducted. Small increases or decreases of feed rates or other parameters are conducted to avoid overshooting. These depend on the individual case, and they may be easily determined by a person of ordinary skill in the art, for example:

the partial pressure of oxidant, preferably oxygen, may be increased by controlling valves 72a and 72b in a manner for example that the valve 72b provides more oxidant; although the total pressure within the reaction chamber 12 is preferably constant, except for the fluctuations needed to measure the pressure drop rate, the total pressure may be increased in a manner that the partial pressure of oxidant is also increased; this is especially useful in case that the two valves 72a and 72b are replaced with a single valve providing line 18 with a mixture of oxidant and inert gas of a constant composition;

the feed rate of hydrocarbon, preferably cyclohexane in the case of production of adipic acid, is increased, especially when the operation takes place close to the limit under which hydrocarbon starvation may be the cause of decrease of the pressure drop rate; this may be arranged by controller 28 through output line 50" which controls valve 50; the feed rate of catalyst, preferably comprising cobalt ions, is increased through valve 54, which is controlled by the computerized controller 28 through output line 54";

the feed rate of promoter is increased through valve 56, which is controlled by the computerized controller 28 through output line 56"; the feed rate of solvent is initially increased through valve 52, which is controlled by the computerized controller 28 through output line 52"; If this has no effect or negative effect, the feed rate of solvent is decreased from its initial value and the effect is also evaluated; if a beneficial effect is achieved, the feed rate of solvent is further decreased within predetermined limits, and so on;

the temperature in the reaction chamber 12 is increased either by means of one or both heat exchangers 44 and 60 through lines 44" and 60", respectively, or by adding more heat directly to the reaction chamber, or removing less heat directly from the reaction chamber, or decreasing the sparging rate of inert gases, such as nitrogen for example, to the reaction chamber.

The opposite procedures may be followed if the pressure drop rate is too high. The controller 28 also compares analytical results of the reaction products, preferably from line 21, and from the aforementioned gas monitors (CO, $CO_2$ and $O_2$), with the influence of the above steps on pressure drop rate, yield, selectivity, conversion, and the like, and optimizes the process according to a predetermined desirable program, depending on the individual occasion, readily designed by a person of ordinary skill in the art.

A preferable type of computerized controller comprises a "learning computer" or a "neuro-computer", the functionality of which is known to the art, and which collects information from different places of the device (for example pressure, temperature, chemical or other analysis, etc.), stores this information along with the result (pressure drop rate, reaction rate, and the like, for example), and it is programmed to use this information in the future, along with other data if applicable, to make decisions regarding the action to be at each instance.

Although the miscellaneous functions are preferably controlled by the computerized controller 28, it is possible, according to this invention, to utilize manual controls for controlling one or more functions.

Oxidations according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products. The carbon dioxide and/or carbon monoxide formed should be taken into account in many occasions for more accurate correlation of pressure drop rate with reaction rate or with reactivity.

Examples include, but of course, are not limited to:

preparation of $C_5$–$C_8$ aliphatic dibasic acids from the corresponding saturated cycloaliphatic hydrocarbons, such as for example preparation of adipic acid from cyclohexane;

preparation of $C_5$–$C_8$ aliphatic dibasic acids from the corresponding ketones, alcohols, and hydroperoxides of saturated cycloaliphatic hydrocarbons, such as for example preparation of adipic acid from cyclohexanone, cyclohexanol, and cyclohexylhydroperoxide;

preparation of $C_5$–$C_8$ cyclic ketones, alcohols, and hydroperoxides from the corresponding saturated cycloaliphatic hydrocarbons, such as for example preparation of cyclohexanone, cyclohexanol, and cyclohexylhydroperoxide from cyclohexane; and preparation of aromatic multi-acids from the corresponding multi-alkyl aromatic compounds, such as for example preparation of phthalic acid, isophthalic acid, and terephthalic acid from o-xylene, m-xylene and p-xylene, respectively.

Regarding adipic acid, the preparation of which is especially suited to the methods and apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Examples of other hydrocarbons, which may be utilized according to this invention are methylated aromatic compounds, such as for example toluene, xylenes, methylated naphthalenes, etc.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All explanations given hereinabove are to be considered as speculative and should not be construed as limiting the breadth of the claims.

What is claimed is:

1. A method of controlling the oxidation of a hydrocarbon to an intermediate oxidation product in a reaction zone comprising the steps of:

(a) feeding a predetermined amount or rate of a gaseous oxidant and a predetermined amount or rate of hydrocarbon into the reaction zone, the reaction zone attaining a first pressure;

(b) measuring a rate of a pressure-drop during the reaction by conducting at least one step of
  (i) allowing the gaseous oxidant to cause a reaction in a manner that the reaction zone attains a second pressure, lower than the first pressure, at least partially resulting from the reaction;
  (ii) allowing the gaseous oxidant to cause a reaction and measuring the pressure drop within a predetermined interval of time;
(c) adjusting the rate of the pressure-drop within a desired range by regulating a parameter in the reaction zone selected from a group consisting of temperature, feed of gaseous oxidant, composition of gaseous oxidant, pressure, feed of hydrocarbon, feed of solvent, feed of catalyst, feed of promoter, and a combination thereof;
(d) repeating steps (a) to (c);
(e) continuing repeating steps (a) to (c).

2. A method as defined in claim 1, wherein the hydrocarbon is a cyclic aliphatic hydrocarbon.

3. A method as defined in claim 2, wherein the cyclic aliphatic hydrocarbon has 5 to 12 carbon atoms.

4. A method as defined in claim 3, wherein the cyclic aliphatic hydrocarbon comprises cyclohexane, and the intermediate oxidation product comprises adipic acid.

5. A method as defined in claim 4, wherein the gaseous oxidant comprises oxygen.

6. A method as defined in claim 1, wherein the gaseous oxidant comprises oxygen.

7. A method as defined in claim 1, wherein the hydrocarbon is a methylated aromatic hydrocarbon.

8. A method as defined in claim 7, wherein the methylated aromatic hydrocarbon is toluene and the intermediate oxidation product is benzoic acid.

9. A method as defined in claim 7, wherein the gaseous oxidant comprises oxygen.

10. A method as defined in claim 8, wherein the gaseous oxidant comprises oxygen.

11. A method as defined in claim 7, wherein the methylated aromatic hydrocarbon is selected from a group consisting of o-xylene, m-xylene, p-xylene, and a mixture thereof, and the intermediate oxidation product is selected from a group consisting of o-phthalic acid, isophthalic acid, terephthalic acid, and a mixture thereof.

12. A method as defined in claim 11, wherein the gaseous oxidant comprises oxygen.

13. A method as defined in claim 1, wherein the hydrocarbon contains at least one ingredient selected from a group consisting of solvent, catalyst, promoter, and a mixture thereof, and it is in an atomized form within the reaction zone.

14. A method as defined in claim 4, wherein the hydrocarbon contains at least one ingredient selected from a group consisting of solvent, catalyst, promoter, and a mixture thereof, and it is in an atomized form within the reaction zone.

15. method as defined in claim 7, wherein the hydrocarbon contains at least one ingredient selected from a group consisting of solvent, catalyst, promoter, and a mixture thereof, and it is in an atomized form within the reaction zone.

16. A method as defined in claim 11, wherein the hydrocarbon contains at least one ingredient selected from a group consisting of solvent, catalyst, promoter, and a mixture thereof, and it is in an atomized form within the reaction zone.

* * * * *